United States Patent [19]

Hodson et al.

[11] 4,025,635

[45] May 24, 1977

[54] CYCLIC SULPHUR COMPOUNDS

[75] Inventors: Harold Francis Hodson, Hayes; John Frederick Batchelor, Beckenham, both of England

[73] Assignee: Burroughs Wellcome Co., Research Triangle Park, N.C.

[22] Filed: Sept. 5, 1973

[21] Appl. No.: 394,424

[30] Foreign Application Priority Data

May 4, 1973 United Kingdom ............ 21174/73
Sept. 6, 1972 United Kingdom ............ 41429/72

[52] U.S. Cl. ........................... 424/269; 260/308 D; 260/327 R; 260/328; 424/45; 424/46; 424/275; 424/276; 424/277
[51] Int. Cl.² ................ C07D 257/04; A61K 31/41
[58] Field of Search ................ 260/308 D; 424/269

[56] References Cited

UNITED STATES PATENTS 3,706,768  12/1972  Bays .................... 424/269

*Primary Examiner*—Frederick E. Waddell
*Attorney, Agent, or Firm*—Donald Brown

[57] ABSTRACT

Certain tricyclic sulphone compounds each of which is substituted in the 1-,2-,3- or 4-position by a carboxyl or (5-tetrazolyl) group and each of which is optionally substituted in the 5-,6-,7- or 8-position by a second carboxyl or (5-tetrazolyl) group or a substituent selected from cyano, halogen, nitro, alkyl, alkoxy, acyl, amino, acylamino, thioalkyl, alkylsulphinyl and alkylsulphonyl, as well as salts, and optionally substituted esters and amides of the carboxyl substituted compounds and alkyl derivatives of the tetrazolyl substituted compounds, are useful for the relief or prophylaxis of allergic conditions.

17 Claims, 20 Drawing Figures

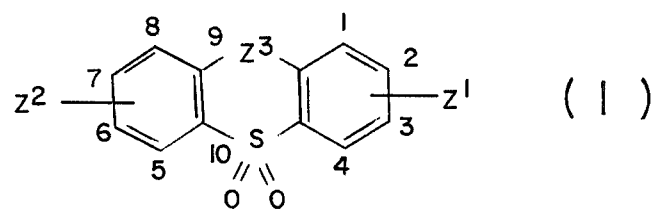
( I )
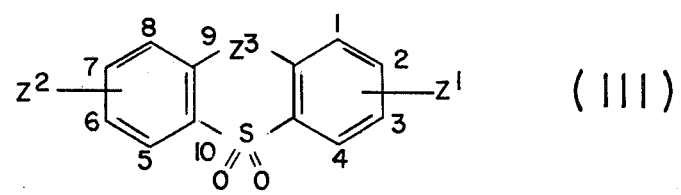
( III )
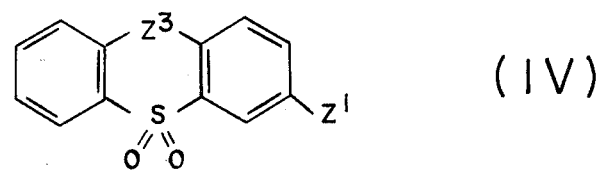
( IV )
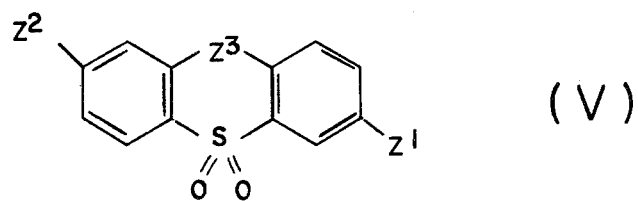
( V )

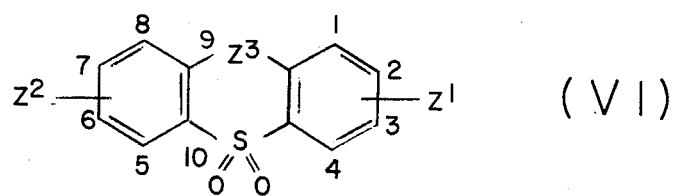
(VI)
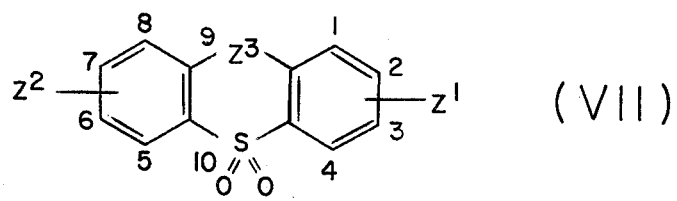
(VII)
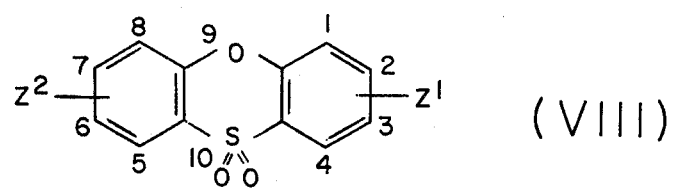
(VIII)
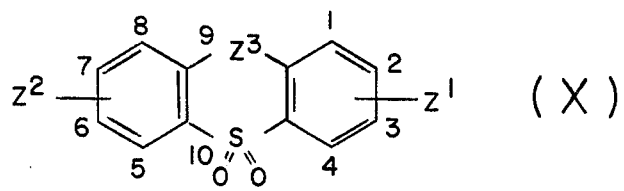
(X)

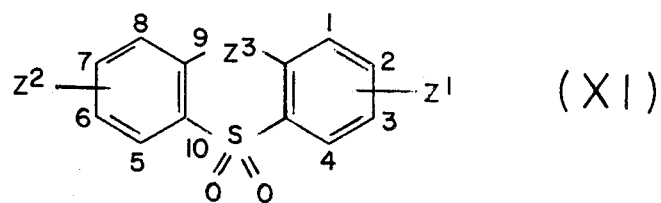
(XI)
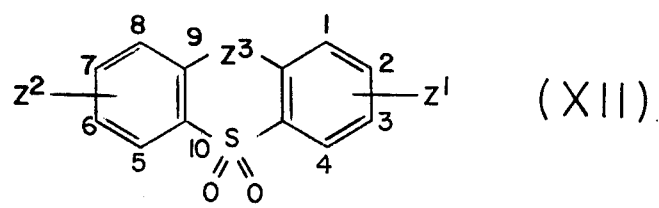
(XII)
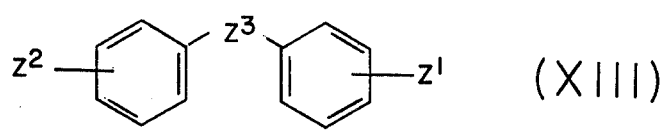
(XIII)
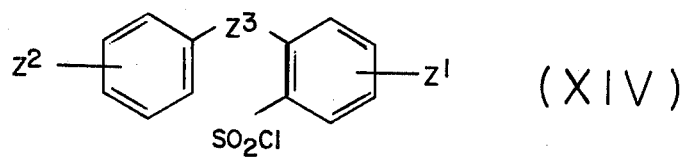
(XIV)

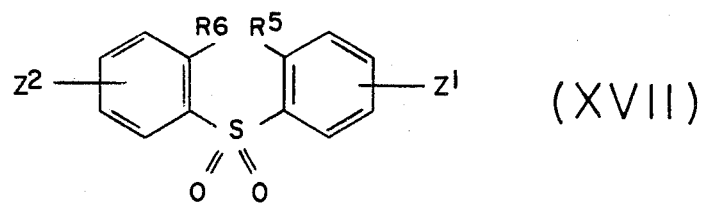
(XVII)
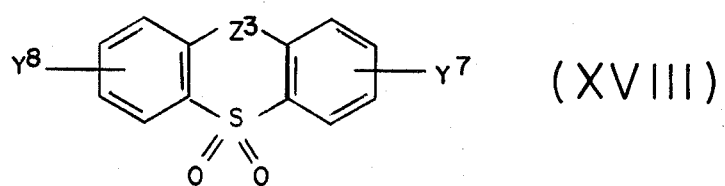
(XVIII)
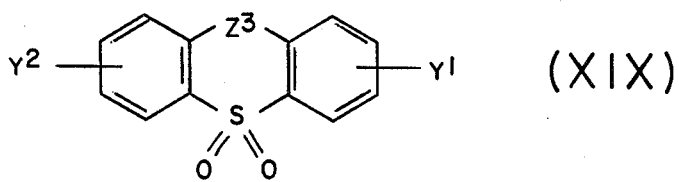
(XIX)
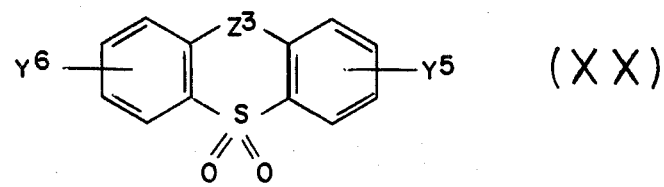
(XX)

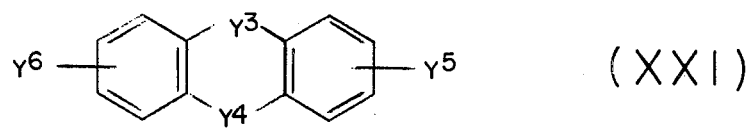
(XXI)
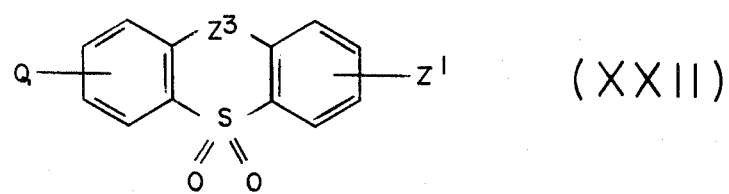
(XXII)
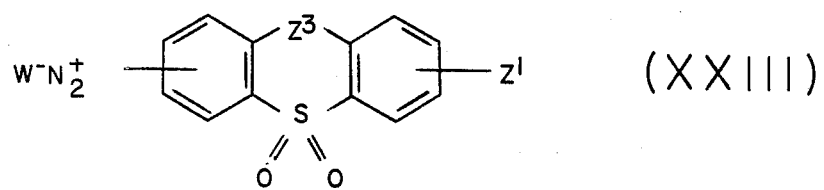
(XXIII)
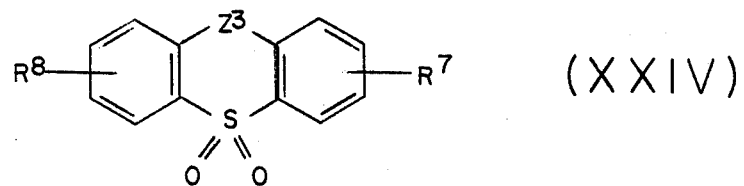
(XXIV)

CYCLIC SULPHUR COMPOUNDS

The invention relates to tricyclic compounds having medicinal properties, the synthesis of the compounds and their adaptation for medicinal use.

It has been found that tricyclic compounds of formula I, as defined hereinbelow, are active in mammals and in in vitro mammalian preparations as inhibitors of allergic reactions associated with reaginic antibodies of the kind responsible for asthma in man, and that this effect is attributable to the suppression of the release of anaphylactic mediators.

In formula I, $Z^1$ is a substituent in the 1-, 2-, 3-, or 4-position and is carboxyl, 5-tetrazolyl, 5-(1-alkyl)tetrazolyl, or 5-(2-alkyl)tetrazolyl in which the alkyl groups have 1 to 6 carbon atoms and are each optionally substituted by a hydroxyl group or a basic or acidic group; $Z^2$ is hydrogen or a substituent in the 5-, 6-, 7-, or 8-position selected from the values of the group $Z^1$ as defined above or is alkylsulphonyl, alkylsulphinyl, thioalkyl, amino, acylamino, nitro, cyano, halogen preferably chlorine or bromine, acyl, alkyl or alkoxy wherein the "alkyl" moiety of each of the acyl, alkyl, alkoxy, thioalkyl, acylamino, alkylsulphinyl and alkylsulphonyl groups has 1 to 6 carbon atoms; and $Z^3$ represents a bond or is oxygen, sulphur, sulphoxide or methylene;

together with salts of said compounds and when at least one of $Z^1$ and $Z^2$ is a carboxyl group, esters and amides of said compounds.

The inhibition activity of the compounds of formula I has been demonstrated (a) in tests using the response of passive cutaneous anaphylaxis (PCA test) in which is measured the skin reaction produced as the result of interaction between specific antigen injected intravenously and cell-fixed reaginic antibody previously injected into the skin of a mammal (see for example Z. Ovary: Fedn. Proc. Am. Soc. exp. Biol. 24, 94 (1965)), (b) by measurement of the amount of histamine released after antigen challenge of peritoneal mast cells from actively sensitised rats (see for example, 1. Acta Pharmacol. et Toxicol. 30, supp. 1 (1971), 2. Thorax, 27/1, 38 (1972)), and (c) by measurement of the histamine released from human chopped lung tissue passively sensitised in vitro with reaginic antibody when challenged with the homologous antigen (Br. Med. J. 3,272 (1968)). The activity of acids of formula I has been demonstrated as described hereinabove using solutions of the anion.

For the sake of convenience, compounds of formula I wherein either of $Z^1$ and $Z^2$ is or both are an alkyl carboxylate group, are hereinafter referred to as 'esters' of formula I. Similarly reference to 'amides' of formula I shall be construed as references to compounds of formula I wherein one or both of $Z^1$ and $Z^2$ is an optionally substituted carboxamide, and references to 'salts' of formula I shall mean salts of formula I wherein one or both of $Z^1$ and $Z^2$ is a salt of the acid.

Pharmaceutically acceptable salts of compounds of formula I include ammonium salts, alkali metal salts such as sodium and potassium salts, alkaline earth salts such as magnesium and calcium salts, and salts of organic bases, for example, amine salts derived from mono-, di-, or tri-lower alkyl or lower alkanolamines such as triethanolamine and diethylaminoethylamine and salts with heterocyclic amines such as piperidine pyridine, piperazine and morpholine. Especially valuable for intravenous and pulmonary administration are water soluble salts, most preferably those having a solubility in water of at least 1 mg/ml.

For the purposes of medicinal administration, the carboxylate salt group may be a salt of any pharmaceutically acceptable cation, since the pharmacological activity of the salts is associated with the anion.

Suitable amides include amides derived from primary or secondary, aliphatic amines such as N-alkyl and N,N-dialkyl amines for example diethylamine. Suitable esters include esters derived from alkylalcohols. The alkyl moieties of the alkyl esters and N-alkyl and N,N-dialkyl carboxamides, preferably each have 1 to 6 carbon atoms, most desirably 1 to 4 carbon atoms.

Each of the alkyl moieties of the esters, alkyltetrazoles and amides is optionally substituted by at least one hydroxy, basic or acidic substituent. Suitable basic substituents include amino groups optionally substituted by one or two alkyl groups and heterocyclic amino groups such as piperidine or morpholine. The esters and amides having basic substituents as well as the amides themselves may be in the form of pharmaceutically acceptable acid addition salts.

Suitable acidic substituents include 5-tetrazolyl groups and carboxyl groups, and their pharmaceutically acceptable salts.

Included within the scope of compounds of formula I are tricyclic compounds of formula III wherein $Z^1$ is a substituent in the 1-, 2-, 3- or 4-position and is carboxyl group, a carboxylate salt group, an alkyl carboxylate group wherein the alkyl moiety has 1 to 6, preferably 1 to 4 carbon atoms, a carboxamide group optionally N-substituted by alkyl having 1 to 6, preferably 1 to 4 carbon atoms, a 5-tetrazolyl group, a 5-tetrazolyl salt group, a 5-(1-alkyl)tetrazolyl group or a 5-(2-alkyl)tetrazolyl group in which the alkyl groups have 1 to 6 carbon atoms and are each optionally substituted by a basic group;

$Z^2$ is hydrogen or a substituent in the 5-, 6-, 7-, or 8-position and has the same values as the group $Z^1$ as defined above or is an alkylsulphonyl group, an alkylsulphinyl group, a thioalkyl group, an amino group, an acylamino group, a nitro group, a cyano group, a halogen atom, an acyl grup, an alkyl group or an alkoxy group wherein the "alkyl" moiety of each of the acyl, alkyl, alkoxy, thioalkyl, acylamino, alkylsulphinyl and alkylsulphonyl groups has 1 to 6 carbon atoms; and $Z^3$ represents a bond or is oxygen, sulphur, sulphoxide or methylene.

Especially preferred sulphone compounds of formula I include tricyclic compound of formula IV wherein $Z^3$ is as defined in formula I, and $Z^1$ is selected from a carboxyl group, a carboxylate salt group, an alkyl carboxylate group having 1 to 6 carbon atoms in the alkyl moiety, a carboxamide group optionally N-substituted by an alkyl group having 1 to 6 carbon atoms, a 5-tetrazolyl group and a 5-tetrazolyl salt group. Within the scope of formula IV, compounds wherein $Z^3$ is oxygen are particularly preferred.

Other preferred compounds of formula I include tricyclic compounds of formula V wherein $Z^3$ is as defined in formula I, and $Z^1$ and $Z^2$ are the same or different and each is selected from a carboxyl group, a carboxylate salt group, an alkyl carboxylate group having 1 to 6 carbon atoms, a carboxamide group optionally N-substituted by an alkyl group having 1 to 6 carbon atoms, a 5-tetrazolyl group, and a 5-tetrazolyl salt group.

Compounds of formula I which show a very high anti-allergic activity on oral administration include 2-(5-tetrazolyl)phenoxathiin-10,10-dioxide, and salts of this compound, especially alkali metal salts including sodium and potassium salts.

Novel compounds of the present invention include tricyclic compounds of formula VI wherein $Z^1$ is a substituent in the 1-, 2-, 3-, or 4-position and is carboxyl, 5-tetrazolyl 5-(1-alkyl)tetrazolyl, or 5-(2-alkyl)-tetrazolyl in which the alkyl groups have 1 to 6 carbon atoms and are each optionally substituted by a hydroxyl group or a basic or acidic group;

$Z^3$ represents a bond or is oxygen, sulphur, sulphoxide or methylene; and $Z^2$ is hydrogen when:

a. $Z^3$ is sulphoxide or methylene and $Z^1$ is as defined above;

b. $Z^3$ is a bond or sulphur or is oxygen and $Z^1$ is carboxyl in the 3- or 2-position, respectively; or c. $Z^3$ is as first defined bove and $Z^1$ is a carboxylate salt group, an alkyl carboxylate group having 2 to 6, preferably 2 to 4 carbon atoms, 5-tetrazolyl, 5-(1-alkyl)tetrazolyl or 5-(2-alkyl)tetrazolyl in which the alkyl groups have 1 to 6 carbon atoms and are each optionally substituted by a hydroxyl group or a basic or acidic group; or $Z^2$ is carboxyl when:

a. $Z^3$ is sulphoxide or methylene and $Z^1$ is as first defined above in this formula; or b. $Z^3$ is as first defined above, $Z^1$ has the same meaning as $Z^2$ and is in the 2- or 3-position provided that when $Z^1$ and $Z^2$ are both carboxyl and $Z^3$ is a bond, $Z^2$ is not in the 6- or 7-position when $Z^1$ is in the 2- or 3-position respectively; or $Z^2$ is a substituent in the 5-, 6-, 7-, or 8-position and is selected from alkylsulphonyl, alkylsulphinyl, thioalkyl, amino, acylamino, nitro, cyano, halogen, preferably chlorine or bromine, acyl, alkyl, or alkoxy wherein the "alkyl" moiety of each of the acyl, alkyl, alkoxy, thioalkyl, acylamino, alkylsulphinyl and alkylsulphonyl groups has 1 to 6 carbon atoms; together with salts of said compounds and when at least one of $Z^1$ and $Z^2$ is a carboxyl group, esters or amides thereof, except for 9-nitro-4-carboxyphenoxathiin-10,10-dioxide, and 8-chloro-2-carboxyphenoxathiin-10,10-dioxide and its methyl ester.

Preferred novel compounds of the present invention include tricyclic compounds of formula VII wherein $Z^1$ is a substituent in the 3-position and is carboxyl, a carboxylate salt group, 5-tetrazolyl, or a 5-tetrazolyl salt group;

$Z^3$ represents a bond or is oxygen, or methylene; and $Z^2$ is a hydrogen when:

a. $Z^3$ is methylene and $Z^1$ is as defined above;

b. $Z^3$ is a bond and $Z^1$ is carboxyl, or a carboxylate salt group; or c. $Z^3$ is as first defined above and $Z^1$ is a carboxylate salt group, 5-tetrazolyl or a 5-tetrazolyl salt group;

$Z^2$ is carboxyl, or a carboxylate salt group when $Z^3$ is methylene and $Z^1$ is as first defined above;

$Z^2$ is selected from the values of $Z^1$ as first above defined when $Z^1$ is in the 3-position and $Z^3$ is as first above defined, provided that when $Z^1$ and $Z^2$ are both carboxyl, $Z^2$ is not in the 7-position when $Z^3$ is a bond; or $Z^2$ is a substituent in the 5-, 6-, 7-, or 8-position and is selected from nitro, chlorine, bromine, and alkyl having 1 to 6 carbon atoms; except for 8-chloro-2-carboxyphenoxathiin-10,10-dioxide and its methyl ester.

Novel phenoxathiin compounds of the present invention include tricyclic compounds of formula VIII wherein $Z^1$ is a substituent in the 2- or 3-position and is carboxyl, 5-tetrazolyl, a 5-tetrazolyl salt group, 5-(1-alkyl)tetrazolyl, or 5-(2-alkyl)tetrazolyl in which the alkyl groups have 1 to 6 carbon atoms and are each optionally substituted by a hydroxyl group or a basic or acidic group, and $Z^2$ is hydrogen or a substituent in the 5-, 6-, 7-, or 8-position selected from the values of the group $Z_1$ defined above or is alkylsulphonyl, alkylsulphinyl, thioalkyl, amino, acylamino, nitro, halogen, preferably chlorine or bromine, acyl, alkyl, or alkoxy wherein the "alkyl" moiety of each of the acyl, alkyl, alkoxy, thioalkyl, acylamino, alkylsulphinyl and alkylsulphonyl groups has 1 to 6 carbon atoms; together with salts of said compounds and when at least one of $Z^1$ and $Z^2$ is a carboxyl group, esters and amides thereof, except for 2-Carboxy-phenoxathiin-10,10-dioxide, and its carboxamide; 8-Chloro-2-carboxyphenoxathiin-10,10-dioxide; 2,8-dicarboxyphenoxathiin-10,10-dioxide; and their methyl esters.

Novel tianthrenes and thioxanthenes of formula I include tricyclic compounds of formula X wherein $Z^1$ is a substituent in the 1-, 2-, 3-, or 4-position and is carboxyl, 5-tetrazolyl, 5-(1-alkyl)tetrazolyl, or 5-(2-alkyl) tetrazolyl in which the alkyl groups have 1 to 6 carbon atoms and are each optionally substituted by a hydroxyl group or a basic or acidic group; $Z^2$ is a hydrogen or a substituent in the 5-, 6-, 7-, or 8-position and is alkylsulphonyl, alkylsulphinyl, thioalkyl, amino, acylamino, nitro, cyano, halogen preferably chlorine or bromine, acyl, alkyl, or alkoxy groups wherein the alkyl moiety of each of the acyl, alkyl, alkoxy, thioalkyl, acylamino, alkylsulphinyl and alkylsulphonyl groups has 1 to 6 carbon atoms; and $Z^3$ is sulphoxide or methylene; together with salts of said compounds and when at least one of $Z^1$ and $Z^2$ is a carboxyl group, esters and amides thereof.

Novel tetrazolyl compounds and their derivatives of the present invention include tricyclic compounds of formula XI wherein $Z^1$ is a substituent in the 1-, 2-, 3-, or 4-position and is 5-tetrazolyl, a 5-tetrazolyl salt group, 5-(1-alkyl) tetrazolyl or 5-(2-alkyl)tetrazolyl in which the alkyl groups have 1 to 6 carbon atoms and are each optionally substituted by a hydroxyl group or a basic or acidic group; $Z^2$ is a hydrogen or a substituent in the 5-, 6-, 7-, or 8-position selected from the values of the group $Z^1$ as defined above or is alkylsulphonyl, alkylsulphinyl, thioalkyl, amino, acylamino, nitro, cyano, halogen preferably chlorine or bromine, acyl, alkyl, or alkoxy wherein the alkyl moiety of each of the acyl, alkyl, alkoxy, thioalkyl, acylamino, alkylsulphinyl and alkylsulphonyl groups has 1 to 6 carbon atoms, carboxyl, a carboxylate salt group, an alkyl carboxylate group wherein the alkyl moiety has 1 to 6, preferably 1 to 4 carbon atoms, or a carboxamide group optionally N-substituted by alkyl having 1 to 6, preferably 1 to 4 carbon atoms; and $Z^3$ represents a bond or is oxygen, sulphur, sulphoxide or methylene.

Novel compounds of the present invention also include the solid tricyclic compounds of formula XII wherein $Z^1$ is a substituent in the 1-, 2-, 3-, or 4-position and is a pharmaceutically acceptable carboxylate salt group, 5-tetrazolyl, a 5-tetrazolyl salt group, 5-(1- alkyl)tetrazolyl or 5-(2-alkyl)tetrazolyl in which the alkyl groups have 1 to 6 carbon atoms and are each optionally substituted by a hydroxyl group or a basic or acidic group; $Z^2$ is a hydrogen or a substituent in the 5-, 6-, 7-, or 8-position selected from the values of the group $Z^1$ defined above or is alkylsulphonyl, alkylsulphinyl, thioalkyl, amino, acylamino, nitro, cyano, halogen preferably chlorine or bromine, acyl, alkyl, or alkoxy wherein the alkyl moiety of the acyl, alkoxy, thioalkyl, acylamino, alkylsulphinyl and alkylsulphonyl groups has 1 to 6 carbon atoms or a carboxyl; and $Z^3$ represents a bond or is oxygen, sulphur, sulphoxide or methylene; and when $Z^2$ includes a carboxyl group, esters or amides thereof; except for 4,6-dicarboxydibenzothiophene-5,5-dioxide disodium salt.

The compounds of formula I may be prepared by known chemical techniques. In general, the methods include cyclisation wherein the central ring is completed by ring closure, oxidation or reduction to complete the structure of the central ring, and formation of one or both of the groups $Z^1$ and $Z^2$ by a variety of techniques. Examples of the preparation of certain compounds of formula I by these methods are described at the end of this specification. These general synthetic procedures are also applicable in some instances to the preparation of intermediates.

The cyclisation preparative methods in general include the formation as the final step of one or both of the bridges of the central ring. For example compounds of formula XIII wherein $Z^1$, $Z^2$ and $Z^3$ are defined in formula (I), may be reacted with chlorosulphonic acid to provide corresponding compounds of formula I, or using chlorosulphonyl compounds of formula XIV wherein $Z^1$, and $Z^2$ and $Z^3$ are defined in formula I, the corresponding compounds of formula I may be prepared, by ring closure using a Lewis acid, for example aluminium chloride with heat.

Thianthrene-10,10-dioxides may also be prepared by reacting a compound of formula XVII wherein $Z^1$ and $Z^2$ are defined in formula I and $R^5$ and $R^6$ are the same or different and each is a leaving group such as halo, nitro or sulphinyl, with sodium sulphide.

These cyclisation reactions may also be used to provide suitable intermediates which can then be converted by methods described below into compounds of formula I. Thus thioxanthene intermediates may be made by cyclisation of 2,2'-dihalophenylmethanes in the presence of sodium sulphide.

Compounds of formula I may also be prepared by oxidation of the corresponding sulphoxides and sulphides to form the sulphones, using for example hydrogen peroxide and acetic acid. In the case of thianthrenes and thianthrene-10-oxides, the thianthrene-9,10,10-trioxides are produced.

Reduction methods may also be employed to make the thioxanthene-10,10-dioxides of formula (I) from the corresponding thioxanthone-10,10-dioxides using appropriate reducing agents such as zinc and hydrochloric acid. Reduction of thianthrene-5,10,10-trioxides with appropriate reducing agents such as zinc and acetic acid yields the corresponding thianthrene-10,10-dioxides.

The compounds of formula I may also be prepared by formation of one or both of the groups $Z^1$ and $Z^2$ as the final step.

Thus in formula I wherein one or both of $Z^1$ and $Z^2$ are tetrazolyl or (1-alkyl)tetrazolyl groups, these compounds may be prepared by reaction of hydrazoic acid or a salt thereof or nitrous acid with an appropriate compound of formula XVIII wherein $Y^7$ is a group $Z^1$ as defined in formula I or a tetrazoyl group precursor and $Y^8$ is a group $Z^2$ as defined in formula (I) or a tetrazolyl group precursor, provided that at least one of $Y^7$ and $Y^8$ is a tetrazolyl group precursor.

When hydrazoic acid or a salt thereof is used, a suitable tetrazolyl group precursor is a group

wherein $R^3$ and $R^4$ together form a bond (nitrile), $R^3$ is hydrogen or alkyl and $R^4$ is alkoxy having 1 to 6 carbon atoms (imidoester), thioalkyl having 1 to 6 carbon atoms (imidothioester), $-NH-NH_2$ (amidrazone), or amino (amidine) or $R^3$ is hydroxy and $R^4$ is amino (amidoxime), or $R^3$ is alkyl and $R^4$ is halogen (imidohalide). In the case of amidoximes and nitriles, only tetrazolyl compounds may be produced and in the case of imidohalides only alkyltetrazolyl compounds may be produced. The reaction is preferably carried out in a polar aprotic liquid medium using a salt of hydrazoic acid.

When nitrous acid is used a suitable tetrazolyl precursor group is a group

wherein $R^3$ is hydrogen or alkyl and $R^4$ is $-NH-NH$ (amidrazone) or $R^3$ is hydrogen and $R^4$ is amino (amidine). In the latter case, reduction of the intermediate nitrosation product, with or without prior isolation, using for example sodium amalgam, is required to give the corresponding tetrazolyl compound.

The tetrazolyl compounds of formula I thus prepared may be isolated as the free acid or as a tetrazolyl salt, and the one converted to the other in known manner and as specifically described below in relation to the carboxylic acids of formula I and their salts.

The 5-(1- and 2-alkyl)tetrazolyl compounds of formula I may be made from the corresponding tetrazolyl compounds of formula I or their salts by alkylation.

The carboxylic acids of formula I, wherein one or both of $Z^1$ and $Z^2$ are carboxyl may be prepared by a variety of methods which include as the final step the formation of the carboxyl group. These compounds may be isolated as the free acid, as salts thereof, or converted to amides or esters of formula I, depending upon the nature of the desired products. Thus they may be prepared by hydrolysis of a compound of formula XIX wherein at least one of $Y^1$ and $Y^2$ is a carboxyl group precursor, such as a nitrile group, trichloromethyl group or a group $COL^1$ wherein $L^1$ is a leaving group, such as a nucleophilic atom or group, for example, a trichloromethyl group, an optionally substituted amino group, a halogen atom or an alkoxy group, when the other is $Z^1$ or $Z^2$ as defined in formula I, as appropriate, or is $Y^1$ as defined above; and $Z^3$ has the meaning defined in formula I. Hydrolysis is conveniently effected by heating a compound of formula XIX with a base or a dilute aqueous mineral acid optionally with an organic acid. For example, one may use dilute sulphuric acid or dilute hydrochloric acid with acetic acid, or a base such as an aqueous alkali metal hydroxide or alkoxide. Basic conditions are, however, undesirable in the preparation of the thioxanthone-10,10-dioxides.

By means of nucleophilic substitution reactions analogous to hydrolysis, for example, alcoholysis and ammonolysis, esters and amides of formula I may be prepared directly from compounds of formula XIX. Thus reaction of a compound of formula XIX with an appropriate alcohol yields an ester of formula I, and reaction with ammonia or an appropriate primary or secondary amine yields an amide of formula I.

The carboxylic acids of formula I and their salts may also be made by oxidation of a compound of formula XX wherein $Y^5$ is an alkyl group, an acyl group or a group $Z^1$ as defined in formula I, $Z^3$ is as defined in formula I, and $Y^6$ is an alkyl group, an acyl group of a group $Z^2$ as defined in formula I provided that at least one of $Y^5$ and $Y^6$ is an alkyl or acyl group. Oxidation of compounds wherein $Y^5$ and/or $Y^6$ are lower alkyl groups may be effected with such conventional oxidising agents as acid or alkaline aqueous potassium permanganate solution; chromium trioxide, for example, with acetic acid or sulphuric acid; oxygen in the presence of a conventional catalyst such as vanadium, cobalt and manganese salts or oxides; or aqueous solutions of dichromate salts.

Oxidation of compounds wherein $Y^5$ and/or $Y^6$ are the groups C(:O)R may be effected with such conventional oxidising agents as chromium trioxide, for example, with acetic acid or sulphuric acid; aqueous solutions of salts of hypochlorous and hypobromous acids in the presence of a base; sodium or potassium dichromate with acetic acid; or nitric acid. These oxidation procedures are advantageously effected with heating in the liquid phase.

If desired, oxidative formation of $Z^1$ and/or $Z^2$ carboxyl groups, the bridging sulphonyl linkage, and $Z^3$ sulphoxide linkage, may be carried out either simultaneously or sequentially. Thus compounds of formula I may be prepared by oxidation with an appropriate oxidising agent of a compound of formula XXI wherein $Y^5$ and $Y^6$ are as defined above in formula XX, $Y^3$ represents a bond or is oxygen, sulphur, sulphoxide, or methylene and $Y^4$ is sulphur, sulphoxide or sulphone provided that at least one of $Y^3$, $Y^4$, $Y^5$ and $Y^6$ is not the same as $Z^3$, sulphonyl, $Z^1$ and $Z^2$ respectively as defined in formula I but is an oxidisable atom or group as defined in this formula.

The compounds of formula I wherein $Z^2$ is other than hydrogen, alkyl, acyl, carboxyl or a derivative thereof or tetrazolyl or a derivative thereof may also be made by formation of the group $Z^2$ as the final step. Such compounds are prepared by introducing an alkylsulphonyl group, alkylsulphinyl group, cyano group, halogen amino group, acylamino group, nitro group, cyano group, halogen atom or alkoxy group into an appropriate compound of formula XXII wherein $Z^1$ and $Z^3$ are as defined in formula I and Q is hydrogen, a leaving group or a precursor, by known methods.

Thus where $Z^2$ is amino, the compounds may be made by reduction of the corresponding nitro compounds which themselves may be made by nitration. The amino compounds may be converted into acylamino compounds by acylation and into the corresponding diazonium compounds of formula XXIII wherein $Z^1$ and $Z^3$ are defined in formula I and W is an anion, for example chloride, bromide or hydrogen sulphate by reaction with nitrous acid. These diazonium compounds may be converted by known methods to the alkoxy compounds (by reaction with water and alkylation of the resulting hydroxy compounds); to the halo compounds (by the Sandmeyer reaction using cuprous bromide or chloride; by the Gattermann reaction using a copper catalyst to produce bromo or chloro compound where W is the chloride or bromide ion; by the Balz-Schiemann reaction using the fluoroborate diazonium salt to produce the fluoro compounds; or by using an alkali metal iodide to produce the iodo compounds); to the nitrile compounds (by modified Sandmeyer or Gattermann reactions using cuprous cyanide or potassium cyanide and copper powder); to thiols and alkylthio compounds (by the Leuckart synthesis by formation of diazoxanthates or diazothioxanthates from the diazo compounds and alkali metal alkyl xanthates or thioxanthates respectively which are decomposed in faintly acid cuprous media to the alkylthio compounds and to thiols on hydrolysis). The thiols may if desired be alkylated to the alkylthio compounds of formula I, and these in turn oxidised to alkylsulphinyl or alkylsulphonyl compounds of formula I.

It will of course be understood that the oxidative formation of the side chains $Z^1$ and/or $Z^2$, the bridging sulphoxide group $Z^3$ and the bridging sulphonyl linkage, may be carried out either simultaneously as a one-pot reaction or sequentially, by the use of appropriate oxidising agents.

In the operation of the foregoing synthetic methods, it will also be understood that where the groups $Z^1$ and $Z^2$ are formed prior to the complete formation of the desired compound, then in some instances $Z^1$ and/or $Z^2$ must be protected from inter-reaction in the final synthetic stage or stages; thus for example when $Z^2$ is an amino group, it may be protected by acylation and the acylamino group subsequently hydrolysed. In other instances it is advisable to form the groups $Z^1$ and/or $Z^2$ as the final synthetic step, if the group(s) would react in the final synthetic stage(s).

Pharmaceutically acceptable salts of tetrazoles or carboxylic acids of formula I are prepared by any conventional method, for example by neutralising the corresponding carboxylic acid or tetrazole with an appropriate Bronsted base, or by double decomposition of a salt of an acid or tetrazole of formula I so as to produce the desired salt of an appropriate pharmaceutically acceptable cation. The carboxylic acid or tetrazole may be either the isolated acid or tetrazole, or may be present in solution in the reaction mixture resulting from a preparation of the compound, for example by such a method as described hereinbefore. Suitable Bronsted bases include organic bases such as ethanolamine, and bases containing ammonium, and alkali metal and alkaline earth metal cations. Double decomposition may be effected advantageously in an anion exchange resin wherein a solution of a salt of an acid or tetrazole of formula I is passed through a cation exchange resin, the resin being charged with a pharmaceutically acceptable cation of the suitable base. Double decomposition may also be effected in ordinary solution between a salt of an acid or tetrazole of formula I and a salt of the desired pharmaceutically acceptable cation.

Specifically, pharmaceutically acceptable salts of carboxylic acids of formula I may be prepared by reaction in a polar medium of a compound of formula XXIV wherein $R^7$ and $R^8$ are the same or different and each is selected from a carboxylic group and a group $Y^1$ as defined hereinbefore in formula XIX, and $Z^3$ has the meaning in formula I, with an appropriate Bronsted base and, when the Bronsted base does not contain a hydroxyl ion, in the presence of water. Examples of appropriate Bronsted bases are alkali and alkaline earth metal oxides and hydroxides for producing corresponding alkali and alkaline earth metal salts of formula I. Preferably the reaction is effected with heating.

Salts of formula I may be isolated from a reaction medium by any conventional process for the isolation of salts from a solution thereof in a polar medium. Thus the salts may be isolated by precipitation of the salt or by removal of the polar medium.

Precipitation of the salt may be effected by mixed solvent crystallisation or by the addition of excess of base or salt thereof so as to produce a concentration of the cation of the salt to be isolated, substantially in excess of the molar ratio thereof in said salt to be isolated.

Mixed solvent crystallisation may be effected by addition, to a solution of a salt of formula I in a polar medium, of a second solvent miscible with the solvent already present and in which second solvent the salt of formula I is less soluble than in the solvent already present.

Removal of the polar medium may be effected by evaporation, for example, by freeze-drying, or by azeotropic distillation.

Desirably the salts of formula I are purified prior to incorporation in a pharmaceutical composition. Purification may be effected by any conventional method. A particularly valuable purification process comprises isolation of a crude solid salt of formula I from a reaction mixture wherein said salt has been produced, by any method for the isolation of salts of formula I as described hereinabove; treatment of an aqueous solution of salt with hydrochloric acid; recovery of the corresponding acid of formula I as solid; neutralisation of the acid of formula I with Bronsted base of which base the cation is the cation of the required salt of formula I; removal of solid impurities by filtration; and isolation of the salt of formula I by a method as described hereinabove.

Conveniently a carboxylic acid of formula I may be purified prior to neutralisation, by recrystallisation or by isolation of a N,N-dimethylformamide adduct and subsequently heating the adduct to drive off the N,N-dimethylformamide. Recrystallisation may be effected using a polar organic solvent optionally containing water, for example, aqueous dimethylformamide, aqueous acetone, or acetic acid may be used.

Esters and amides of acids of formula I may be prepared by any conventional method including esterification of the acid or acid chloride with an alkyl or aryl alcohol to yield the corresponding alkyl or aryl ester respectively and reaction of the acid or acid chloride with ammonia or an amine to yield the corresponding amide or substituted amide respectively. Compounds of formula I where $Z^1$ and $Z^2$ are different and are chosen from acid, ester, amide and salt functions, may be prepared by the above methods, and by partial hydrolysis, where appropriate.

The compounds of formula I are useful in the treatment or prophylaxis of mammalian allergic conditions such as asthma and other allergic chest conditions, hay fever (allergic rhinitis), conjunctivitis, urticaria and eczema. In particular they are of value in reaginic mediated Type I hypersentitivity asthma ('extrinsic asthma') and the so-called 'intrinsic asthma' in which no sensitivity to extrinsic antigen can be shown.

The magnitude of a prophylactic or therapeutic dose of compound of formula I will of course vary with the nature and the severity of the allergic condition to be treated and with the particular compound of formula I and its route of administration. In general the dose range lies within the range of 2 $\mu$g. to 100 mg. per Kg. body weight of a mammal.

In the case of an allergic condition as defined hereinbefore, for example, allergic asthma, a suitable dosage is from 5 $\mu$g. to 0.5 mg., preferably from 20 $\mu$g. to 0.2 mg., for example about 0.1 mg., of a compound of formula I, per Kg. of bodyweight of the patient undergoing treatment, when pulmonary administration as described hereinafter is employed. In the case where a composition for intravenous administration is employed a suitable dosage range is from 0.2 to 10 mg. (preferably 1 to 5 mg.) of a compound of formula I per Kg. of bodyweight of patient, and in the case where an oral composition is employed a suitable dosage range is from 1 to 50 mg. of a compound of formula I per Kg. of bodyweight of a patient, preferably from 10 to 40 mg/Kg.

In the case where a composition for nasal and ocular administration is employed, for example, in the treatment of allergic rhinitis, a suitable dose is from 0.5 to 25 mg. of a compound of formula I per patient.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular and intravenous) administration, although the most suitable route in any given case will depend on the nature and severity of the condition being treated, and on the nature of the active ingredient. They may be conveniently presented in unit dosage form and prepared by any of the methods well known in the art of pharmacy.

Pharmaceutical compositions of the present invention suitable for oral administration may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more accessory ingredients. In general the compositions are prepared by uniformly and intimately admixing the active ingredient with liquid carriers or finely divided solid carriers or both, and then, if necessary, shaping the product into the desired presentation. For example a tablet may be prepared compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 50mg. to 500mg. of the active ingredient, and each cachet or capsule contains from 50 to 500 mg. of the active ingredient.

A particularly valuable form of a pharmaceutical composition of the present invention, for use in the treatment of allergic asthma, is a composition suitable for pulmonary administration via the buccal cavity; although, of course conditions other than allergic asthma may also be treated by pulmonary administration of the composition.

Preferably the composition is such that particles having a diameter of 0.5 to $7\mu$ most preferably 1 to $6\mu$, containing active ingredient, are delivered into lungs of a patient. This ensures that a maximal amount of active ingredient is administered to the alveolar sacs of the lungs and retained therein thus producing a maximal effect in the patient. Such compositions are most preferably in the form of dry powders for administration from a powder inhalation device or self-propelling powder-dispensing compositions.

Most preferably the powders of the pulmonary compositions as described hereinabove and hereinbelow comprise particles containing active ingredient of which particles at least 98% by weight have a diameter greater than $0.5\mu$ and at least 95% by number have a diameter less than $7\mu$. Most desirably at least 95% by weight of the particles have a diameter greater than $1\mu$ and at least 90% by number of the particles have a diameter less than $6\mu$.

The compositions in the form of dry powders preferably comprise particles containing the solid active ingredient, the particles having a diameter of 0.5 to $7\mu$ most preferably 1 to $6\mu$. Preferably these compositions include a solid diluent in the form of a fine powder. These compositions may be conveniently presented in a pierceable capsule of a pharmaceutically acceptable material, for example gelatin. Such compositions may be conveniently prepared by comminution of solid active ingredient optionally with a solid diluent. If desired the resulting powder may be filled into a pierceable capsule of a pharmaceutically acceptable material.

Other valuable forms of a composition of the present invention that are suitable for pulmonary administration are self-propelling compositions. These self-propelling compositions may be either powder-dispensing compositions or compositions dispensing the active ingredient in the form of droplets of a solution or suspension.

Self-propelling powder-dispensing compositions preferably comprise dispersed particles of solid active ingredient, having a diameter of 0.5 to $7\mu$ most preferably 1 to $6\mu$ and a liquid propellant having a boiling point of below 65° F at atmospheric pressure. The liquid propellant may be any propellant known to be suitable for medicinal administration and may comprise one or more lower alkyl hydrocarbons, or halogenated lower alkyl hydrocarbons, or mixtures thereof. Chlorinated and fluorinated lower alkyl hydrocarbons are especially preferred as propellant. Generally the propellant may constitute 50 to 99.9% w/w of the composition whilst the active ingredient may constitute 0.1 to 20% w/w, for example, about 2% w/w, of the composition.

The pharmaceutically acceptable carrier in such self-propelling compositions may include other constituents in addition to the propellant, in particular a surfactant or a solid diluent or both. Surfactants are desirable in preventing agglomeration of the particles of active ingredient and in maintaining the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with aliphatic polyhydric alcohols, for instance, sorbitan monooleate and sorbitan trioleate, known commercially as 'Span $\lambda$' (Trade Name) and "Span 85" (Trade Name). The liquid non-ionic surfactant may constitute up to 20% w/w of the composition, though preferably it constitutes below 1% w/w of the composition. Suitable solid anionic surfactants include alkali metal, ammonium and amine salts of dialkyl sulphosuccinate, where the alkyl groups have 4 to 12 carbon atoms, and alkylbenzene sulphonic acid where the alkyl group has 8 to 14 carbon atoms. The solid anionic surfactants may constitute up to 20% w/w of the composition, though preferably below 1% w/w of the composition.

Solid diluents may be advantageously incorporated in such self-propelling compositions where the density of the active ingredient differs substantially from the density of the propellant; also in order to help to maintain the active ingredient in suspension. The solid diluent is in the form of a fine powder, preferably having a particle size of the same order as that of the particles of active ingredients. Suitable solid diluents include sodium chloride and sodium sulphate.

Compositions of the present invention may also be in the form of a self-propelling composition wherein the active ingredient is present in solution. Such self-propelling compositions may comprise an active ingredient, propellant and co-solvent, and advantageously an antioxidant stabiliser. The propellant is one or more of those already cited above. Co-solvents are chosen for their solubility in the propellant, their ability to dissolve the active ingredient, and for their having the lowest boiling point consistent with these above-mentioned properties. Suitable co-solvents are lower alkyl alcohols and ethers and mixtures thereof. The co-solvents may constitute 5 to 40% w/w of the composition, though preferably less than 20% w/w of the composition.

Antioxidant stabilisers may be incorporated in such solution-compositions to inhibit deterioration of the active ingredient and are conveniently alkali metal ascorbates or bisulfites. They are preferably present in an amount of up to 0.25% w/w of the composition.

Such self-propelling compositions may be prepared by any method known in the art. For example the active ingredient either as particles as defined hereinbefore in suspension in a suitable liquid or in up to 20% w/v solution in an acceptable co-solvent as appropriate, is mixed with any other constituents of a pharmaceutically acceptable carrier. The resulting mixture is cooled and introduced into a suitable cooled container and propellant is added thereto in liquid form; and the container is sealed.

Alternatively, such self-propelling compositions may be prepared by mixing the active ingredient either in particles as hereinbefore defined or in 2 to 20% w/v alcohol or aqueous solution as appropriate, together with the remaining constituents of the pharmaceutically acceptable carrier other than propellant; introducing the resulting mixture, optionally with some propellant, into a suitable container; sealing the container;

and injecting propellant under pressure into the container at ambient temperature through a valve which comprises a part of the container and is used to control release of the composition from it. Desirably the container is purged by removing air from it at a convenient stage in the preparation of the self-propelling composition.

A suitable container for a self-propelling composition, is one provided with a manually operable valve and being constructed of aluminum, stainless steel or reinforced glass. The valve should of course be one having the desired spray characteristic, that is, the spray issuing from the valve should have the characteristics of particle size and hereinbefore defined. Advantageously the valve is of the metered type, that is a valve of the type which delivers a fixed amount of composition on the occasion of each operation of the valve, for example, about 50 or 100 microliters of composition in each delivery.

Compositions of the present invention may also be in the form of aqueous or dilute alcoholic solution, optionally a sterile solution, of the active ingredient for use in a nebuliser or atomiser, wherein an accelerated air stream is used to produce a fine mist consisting of small droplets of the solution. Such compositions usually contain a flavouring agent such as saccharin sodium and a volatile oil. A buffering agent such as sodium phosphate; an antioxidant such as sodium metabisulfite; and a surface active agent may also be included in such a composition. Desirably such a composition should contain a preservative such as methylhydroxybenzoate.

Compositions of the present invention suitable for parenteral administration conveniently comprise sterile aqueous solutions of the active ingredient, which solutions are preferably isotonic with blood of a patient under treatment. These are preferably administered intra-venously, although administration may also be effected by means of subcutaneous or intra-muscular injection. Such compositions may be conveniently prepared by dissolving solid active ingredient in water to produce an aqueous solution, and rendering said solution sterile and isotonic with human blood.

Pharmaceutical compositions of the present invention suitable for topical use include compositions suitable for administration to the skin, eyes, nose and mouth.

Compositions for use on the skin include lotions and creams comprising liquid or semi-solid emulsions, either oil-in-water or water-in-oil, which preferably contain from 0.2 to 5% w/v of the active ingredient. Ointments comprising 0.2 to 5% w/v of the active ingredient dissolved or dispersed in a semi-solid basis may also be used for topical administration to the skin. Conveniently the semi-solid basis contains liquid or semi-solid hydrocarbons, animal fat, wool alcohol or a macrogol, possibly with an emulsifying agent. Desirably the creams and ointments should contain a preservative such as methyl hydroxybenzoate.

Compositions for administration to the eye include eye drops comprising the active ingredient in aqueous or oily solution, preferably at a concentration of 0.2 to 5% w/v. Such solutions are desirably fungistatic and bacteriostatic and are preferably prepared sterile. Compositions for administration to the eye also include eye ointments which preferably comprise the same concentration of active ingredient, conveniently in the form of a salt, either dissolved in one of the ingredients of the semi-solid basis of the ointment or as a finely divided suspension therein.

Compositions suitable for administration to the nose include powder, self-propelling and spray compositions similar to those already described under compositions suitable for pulmonary administration but having when dispersed, a somewhat larger particle size of the order of 10 to 200 microns. In the case of self-propelling solution and spray compositions this effect may be achieved by choice of a valve having the desired spray characteristics i.e., being capable of producing a spray having the desired particle size or by incorporating the medicament as a suspended powder of controlled particle size. Thus the composition instead of passing into the lungs is largely retained in the nasal cavity. Other compositions suitable for nasal administration include a coarse powder having a particle size of 20 to 500 microns which is administered in the manner in which snuff is taken i.e., by rapid inhalation through the nasal passage from a container of the powder held close up to the nose. Another composition suitable for nasal administration is nasal drops comprising 0.2 to 5% w/v of the active ingredient in aqueous or oily solution.

Compositions suitable for topical administration in the mouth include lozenges comprising 10 to 100 mg. of the active ingredient in a flavoured basis, usually sucrose and acacia or tragacanth; and pastilles comprising 10 to 100mg. of the active ingredient in an inert basis such as gelatin and glycerin; or sucrose and acacia.

Other therapeutic ingredients suitable for inclusion in the hereinbefore described compositions, especially in the case of those compositions intended for use in the treatment of allergic asthma, include bronchodilators. Any bronchodilator may be used in such a composition although particularly suitable bronchodilators are isoprenaline, adrenaline, orciprenaline, isoethanine and physiologically acceptable acid addition salts thereof, especially isoprenaline sulphate. Conveniently the bronchodilator is present in the composition in an amount of 0.1 to 50% w/w of the weight of active ingredient present.

Included within the scope of the present invention, but in no way limited thereto, are the following specific features:

1. A compound of formula I as defined hereinabove, where novel.
2. The synthesis of compounds of formula I as defined hereinabove, by any method known in the art for preparing them and compounds of analogous chemical structure.
3. Pharmaceutical compositions comprising a compound of formula I as defined hereinabove in association with a pharmaceutically acceptable carrier therefor.
4. The preparation of pharmaceutical compositions comprising a compound of formula I as defined hereinabove as an active ingredient, by any conventional method, including admixture of the ingredients.
5. A method of treatment or prophylaxis of mammalian allergic conditions comprising administration of a therapeutic or prophylactic dose respectively, of a compound of formula I as defined hereinabove.

The following preparations and examples illustrate the methods for preparing compounds in accordance with the present invention, as well as compounds and compositions of the present invention. In the examples and preparations, all temperatures are in degrees Celsius. Where melting points are not given for compounds of formula I, the compounds decompose at temperatures below their melting points and/or their melting points are at temperatures above those readily determinable by conventional techniques. In these preparations and examples, the numbering of substituent positions in the tricyclic nucleus used is not necessarily the same as that used in formula I, but is the standard numbering in respect of the particular tricyclic nucleus concerned, as given in the "Ring Index", IInd Edition, Published by The American Chemical Society, 1960. This standard numbering also applies in respect of the individual named compounds disclosed hereinbefore.

REFERENCE PREPARATION 1
2-CARBOXYDIBENZOTHIOPHENE-5,5-DIOXIDE

A. Preparation of 2-Acetyldibenzothiophene

Dibenzothiophene (18.4g.) and anhydrous aluminium chloride (13.3g.) were mechanically stirred in carbon disulphide (100 ml.) while acetyl chloride (7.85g.) in carbon disulphide (20 ml.) was added dropwise over 0.5 hr. The temperature of the mixture rose to 30° C. After a total of 4 hr. stirring the mixture was poured on to ice and extracted with chloroform. The extract was washed with sodium bicarbonate solution, dried with magnesium sulphate, and evaporated. The residue was distilled under vacuum and a fraction, b.pt. 160°–180° C at 0.6 mm. Hg, was extracted by boiling with ether, and the residue recrystallised twice from methanol to give colourless crystals of 2-acetyldibenzothiophene m.pt. 97°–100° C.

B. Preparation of Dibenzothiophene-2-carboxylic acid

2-Acetyldibenzothiophene (2.24g.), sodium hypochlorite solution, (47ml. containing 5.7% available chlorine), Normal sodium hydroxide solution (50 ml.) and dioxan (50 ml.), were heated on a steam bath with stirring for 5 hr. The mixture was acidified with excess hydrochloric acid, and the precipitated colourless solid filtered off, washed with water, and recrystallised twice from acetic acid to give dibenzothiophene-2-carboxylic acid, m.pt. 281°–283° C.

C. Preparation of
2-Carboxydibenzothiophene-10,10-dioxide

A mixture of dibenzothiophene-2-carboxylic acid (0.70g), 30% hydrogen peroxide (3.0 ml.) and acetic acid (30 ml.) was boiled under reflux for 2.5 hr. The solid product which separated on cooling was filtered off, recrystallised from dimethylformamide, and dried at 110° C, to give 2-Carboxydibenzothiophene-10,10-dioxide, m.pt. > 350° C.

Found: C 59.78%, H 3.38%. $C_{13}H_8O_4S$ requires C 59.98%, H 3.10%.

REFERENCE PREPARATION 2
2,8-Dicarboxyphenoxathiin-10,10-dioxide

A. Preparation of
2,8-Diacetylphenoxathiin-10,10-dioxide 2,8-Diacetylphenoxathiin (10.0g.) was boiled under reflux for 1 hr. with glacial acetic acid (200 ml.) and 30% hydrogen peroxide (30 ml.). The solution was allowed to cool, and the colourless platelets which crystallised out were filtered off and dried to yield 2,8-diacetylphenoxathiin-10,10-dioxide, m.pt. 219°–220° C.

B. Preparation of 2,8-Dicarboxyphenoxathiin-10,10 dioxide 2,8-Diacetylphenoxathiin-10,10-dioxide (10.9g.), acetic acid (480 ml.) and chromium trioxide (20.0g.) were boiled under relux for 45 min. On cooling the product crystallised out and was filtered off, washed with water, and recrystallised from aqueous dimethylformamide to yield colourless needles of 2,8-dicarboxyphenoxathiin-10,10-dioxide, m.pt. 399°–401° C. Thin layer chromatography indicated slight contamination with monocarboxylic acid.

Found: C 53.16%; H 2.60%; S. 9.65%. $C_{14}H_8O_7S$ requires: C 52.51%; H 2.52%; S 9.98%.

REFERENCE PREPARATION 3
2-Methoxycarbonylphenoxathiin-10,10-dioxide 2-carboxyphenoxathiin-10,10-dioxide (0.50g.) in carbon tetrachloride (25ml.) and thionyl chloride (2.0 ml.) was boiled under reflux for 2 hr. The solvent was evaporated and methanol (20. ml.) added. The mixture was boiled under reflux for 20 min., and cooled, whereupon 2-methoxycarbonylphenoxathiin-10,10-dioxide crystallised out and was filtered off and dried, m.pt. 160° C.

Found: C 57.66%; H 3.39%. $C_{14}H_{10}O_5$ requires: C 57.92%; H 3.47%.

REFERENCE PREPARATION 4
2-Carboxyphenoxathiin-10,10-dioxide

A. Preparation of 2-acetylphenoxathiin

Phenoxathiin (22.9 g) and acetyl chloride (8.8 ml) were dissolved in carbon disulphide (120 ml) and mechanically stirred while aluminum chloride (15.5 g) was added in small portions. The red mixture was stirred for 2 hr. at room temperature, then boiled under reflux on the water bath for a further 22¼ hr. The mixture was cooled and poured on to ice and hydrochloric acid, and the precipitated product filtered off, washed with water, and recrystallised once from ethanol and twice from petroleum ether (b.p. 80°–100° C) to give the product m.p. 112° C.

B. Preparation of phenoxathiin-2-carboxylic acid

A mixture of 2-acetylphenoxathiin (4.80 g), sodium hypochlorite solution (95 ml; 5.7% available chlorine), 4% sodium hydroxide solution (100 ml) and dioxan (100 ml) was mechanically stirred on the steam bath for 5 hrs. The solution was poured on to ice and excess hydrochloric acid with stirring. The white precipitate was filtered off and dissolved in hot 4% sodium hydroxide solution (40 ml) and filtered. The sodium salt of the required acid crystallised from the filtrate on cooling and was filtered off, dissolved in boiling water, and the acid precipitated by addition of excess hydrochloric acid. It was filtered off and recrystallised from acetic acid, m.p. 253° C.

C. Preparation of
2-carboxyphenoxathiin-10,10-dioxide

Phenoxathiin-2-carboxylic acid (3.50 g) was boiled with 30% hydrogen peroxide (10 ml) in acetic acid (100 ml) for 2.5 hr. On cooling the product crystallised out and was filtered off and dried, m.p. 286° C.

EXAMPLE

1—3-(5-Tetrazolyl)thioxanthene-10,10-dioxide

A. Preparation of 3-(5-Tetrazolyl)thioxanthone-10,10-dioxide

3-Carboxythioxanthone-10,10-dioxide was treated with thionyl chloride to produce the acid chloride which, after reaction with aqueous ammonia, gave 3-carbamoylthioxanthone-10,10-dioxide m.p. 292° C. A solution of the carboxamide in dimethylformamide gave, after treatment with thionyl chloride, thioxanthene-3-cyano-9-oxo-10,10-dioxide, m.p. 282°–283° C. Treatment of the cyano compound with sodium azide and ammonium chloride in dimethylformamide gave 3-(5-Tetrazolyl)thioxanthone-10,10-dioxide which after recrystallisation had a m.p. of 260°–262° C.

B. Preparation of 3-(Tetrazolyl)thioxanthene-10,10-dioxide

To 3-(5-tetrazolyl)thioxanthone-10,10-dioxide (1.25g.), zinc wool (2.50g.) and mercuric acetate (0.10g.) was added acetic acid (25 ml.) and concentrated hydrochloric acid (25 ml.), and the mixture boiled under reflux for 2hr. After this time a further amount of hydrochloric acid (1.5ml.) was added and the mixture boiled for a further 4 hr., filtered while hot, cooled, the diluted with water. The crude product was filtered off, recrystallised three times from methanol, and dried at 80° C in vacuo to give 3-(5-tetrazolyl)thioxanthene-10,10-dioxide m.pt. 233° C with decomposition.

Found: C 55.91%; H 3.48%; N 18.94%. $C_{14}H_{10}N_4O_2S$ requires C 56.23%; H 3.38%; N 18.79%.

EXAMPLE 2 — 3-Carboxythianthrene-5,5-dioxide

A. 4-Chloro-3-mercaptobenzoic acid

3-Amino-4-chlorobenzoic acid (34.3g) was added to 5N hydrochloric acid (120 ml) and cooled to 0° C. To the stirred suspension was added a solution of sodium nitrite (14.5g) in water (35 ml) over 30 min. with the temperature maintained at 0° to 5° C. The yellow diazonium solution, containing some suspended solid was added to a solution of potassium ethyl xanthate (37.5g) in water (60 ml), containing 0.2g nickel chloride, at 45°–50° C. Nitrogen evolution occurred and the yellow solid which precipitated at first decomposed to a red oil which then solidified. When the addition was complete, the mixture was heated to 70° C., cooled, and the red solid filtered off and washed with water. It was then boiled with a solution of potassium hydroxide (60 g) in water (300 ml) for 2 hr., cooled, filtered and acidified with excess hydrochloric acid. Thin-layer chromatography indicated the presence of 2 components in the precipitated creamy solid. Recrystallisation from acetic acid yielded a by-product, m.p. 240°–290° C., and dilution of the recrystallisation liquors gave a solid which was recrystallised from aqueous ethanol yielding mainly 4-chloro-3-mercapto-benzoic acid, m.p. 209°–211° C.

B. 4-Chloro-3-(o-nitrophenylthio)benzoic acid

Sodium (2.93g) was dissolved in dry methanol (100 ml), 4-chloro-3-mercaptobenzoic acid (12.0g) added, and the solution evaporated to dryness. The residue was dissolved in dimethylsulphoxide (130 ml) and o-chloronitrobenzene (10.0g) added. The mixture was heated on the steam bath for 30 min., poured into water, and extracted with chloroform (2×75 ml). The aqueous solution was acidified with hydrochloric acid and the precipitated 4-chloro-3-(o-nitrophenylthio)-benzoic acid filtered off, washd with water, and recrystallised from acetic acid, m.p. 261°–262° C.

C. 4-Chloro-3-(o-nitrophenylsulphonyl)benzoic acid

4-Chloro-3-(o-nitrophenylthio)benzoic acid (13.1g), acetic acid (250 ml) and 30% hydrogen peroxide (17.5 ml) were boiled together under reflux for 1 hr. Two further (17.5 ml) portions of hydrogen peroxide were added, refluxing 1 hr. after each addition, and the reaction mixture then cooled, diluted with water and 4-chloro-3-(o-nitrophenylsulphonyl)benzoic acid filtered off, washed with water and dried, m.p. 242°–246° C. A sample recrystallised from methanol had m.p. 244°–246° C.

D. 3-(o-Aminophenylsulphonyl)-4-chlorobenzoic acid

A mixture of 4-chloro-3-(o-nitrophenylsulphonyl)-benzoic acid (1.71g), stannous chloride (3.12g), concentrated hydrochloric acid (6.6 ml) and acetic acid (25 ml) was heated on the steam bath for 30 min., cooled, and diluted with water. 3-(o-Aminophenylsulphonyl)-4-chlorobenzoic acid was filtered off, washed with water and dried, m.p. 235°–238° C, providing on recrystallisation from acetic acid, m.p. 246°–248° C.

E. 3-Carboxythianthrene-5,5-dioxide 3-(o-Aminophenylsulphonyl)-4-chlorobenoizc acid (6.00 g) was stirred with concentrated hydrochloric acid (8.0 ml) and water (12.0 ml) and treated at 0°–5° C. with a solution of sodium nitrite (1.50g) in water (30 ml) over 30 min. After a further 15 min. stirring the suspension was pipetted into a solution of potassium ethyl xanthate (10.2g) and sodium hydroxide (1.60g) in water (50 ml) at 45°–50° C. Vigorous nitrogen evolution took place. After the addition was complete the now clear solution was heated to boiling and further sodium hydroxide (3.20g) was added. Boiling was continued for a further 20 min., and the solution then cooled, filtered and acidified with hydrochloric acid. The solid precipitated acid was filtered off, washed with water, and recrystallised from acetic acid to give 3-carboxythianthrene-5,5-dioxide, m.p. 297°–304° C; on further recrystallisation from ethanol it had m.p. 302°–305° C.

Found: C 53.35%; H 2.94%; $C_{13}H_8O_4S_2$ requires C 53.43% H 2.76%

EXAMPLE 3 — 3-(5-Tetrazolyl)thianthrene-5,5-dioxide

A. 3-Cyanothianthrene-5,5-dioxide

3-Carboxythianthrene-5,5-dioxide (0.70g), thionyl chloride (10.0 ml) and dimethylformamide (1 drop) were boiled together under reflux for 30 min; then evaporated to dryness to give the acid cloride, which was treated with 0.880 ammonia (10.0 ml), warmed to 50° C., and the solid amide filtered off, washed with water and dried. To the amide, dissolved in dimethylformamide (15 ml) and cooled to −60° C., was added thionyl chloride (1.5 ml) and the solution allowed to stand at 0° C. in an ice-bath for 20 min. It was then poured on to ice and the solid 3-cyanothianthrene-5,5-dioxide filtered off, washed with water, and dried, m.p. 210°–211° C.

B. 3-(5-Tetrazolyl)thianthrene-5,5-dioxide

3-Cyanothianthrene-5,5-dioxide (0.55g), sodium azide (0.36g), ammonium chloride (0.30g) and dimethylformamide (15 ml) were heated together at 130°–135° C. for 3 hr. The mixture was cooled, poured into dilute hydrochloric acid, and the oily precipitated product extracted into chloroform and washed with water. On standing, 3-(5-tetrazolyl)thianthrene-5,5-dioxide crystallised out, m.p. 233° C. (decomposition).

Found: C 49.19%; H 2.58%; N 17.55%. $C_{13}H_8N_4O_2S_2$ requires: C 49.37%; H 2.55%; N 17.72%.

EXAMPLE 4 —
2-Carboxy-8-methylphenoxathiin-10,10-dioxide

A. 4,4'-Dimethyldiphenyl ether p-Bromotoluene (51g), p-cresol (33g) and potassium hydroxide (18.5 g) were mechanically stirred on a steam bath for 30 min., then heated at 190° C. for 1 hr. Copper bronze (2.0g) was added and the heating continued for a further 1 hr. at 190° C., then 220° to 230° C. for 2.5 hr. After cooling, the residue was extracted into chloroform, filtered, and the extract washed with water, dried, evaporated and crystallised from ethanol to yield 4,4'-dimethyldiphenyl ether, m.p. 49°–50° C.

B. 2,8-Dimethylphenoxathiin 4,4'-Dimethyldiphenyl ether (28.0g), sulphur (4.40g) and aluminium chloride were stirred and heated together at 75°–80° C. for 1 hr. and 100° C. for 4 hr. The mixture was cooled and poured into hydrochloric acid. The oily solid product was separated, triturated with methanol and filtered off, and the product, 2,8-dimethylphenoxathiin, recrystallised from methanol, m.p. 69°–70° C.

C. 2,8-Dimethylphenoxathiin-10,10-dioxide 2,8-Dimethylphenoxathiin (5.90g) was dissolved in boiling acetic acid (30 ml) and 30% hydrogen peroxide (10.0 ml) was added dropwise. After 2 hours boiling under reflux the resulting solution was filtered while boiling, and on cooling 2,8-dimethylphenoxathiin-10,10-dioxide crystallised out and was filtered off and dried, m.p. 175°–176° C.

D. 2-Carboxy-8-methylphenoxathiin-10,10-dioxide 2,8-Dimethylphenoxathiin-10.10-dioxide (5.30g) was dissolved in boiling acetic acid (100 ml) and chromium trioxide (5.70g) in acetic acid (50 ml) added. The solution was boiled under reflux for 6 hr. On cooling starting material (2.38g), m.p. 177°–178° C. crystallised out and was filtered off, and dilution with water yielded further solid material (2.00g) which was warmed with 5% sodium bicarbonate solution and filtered, giving 1.35g starting material m.p. 170°–174° C. Acidification of the filtrate with hydrochloric acid gave 2-carboxy-8-methylphenoxathiin-10,10-dioxide, which was filtered off and washed with water, m.p. 274°–276° C.

Found: C, 57.69%; H, 3.35%. $C_{14}H_{10}O_5S$ requires C, 57.94%; H, 3.47%.

EXAMPLE 5 —
8-Methyl-2-(5-tetrazolyl)phenoxathiin-10,10-dioxide

2-Carboxy-8-methylphenoxathiin-10,10-dioxide (0.22g), thionyl chloride (4.0 ml) and dimethylformamide (1 drop) were boiled together under reflux for 30 min., and evaporated to dryness. The residual acid chloride was treated with 0.880 ammonia (10 ml) and the mixture allowed to stand overnight. The solid amide was then filtered off, dried, dissolved in hot dimethylformamide (5.0 ml), and cooled to −60° C. Thionyl chloride (0.70 ml) was added and the mixture stood at 0° C. in an ice-bath. Dilution with iced water precipitated 2-cyano-8-methylphenoxathiin-10,10-dioxide, and the dried crude nitrile, m.p. 263°–267° C., was heated with sodium azide (0.12g), ammonium chloride (0.10g) and dimethylformamide at 125°–130° C. for 4 hr. The reaction mixture was cooled, diluted with 0.1N sodium hydroxide solution (20 ml), and extracted with chloroform (20 ml). Acidification of the aqueous solution precipitated 8-methyl-2-(5-tetrazolyl)phenoxathiin-10,10-dioxide which was filtered off, washed with water and dried, m.p. 233° C., with decomposition.

Found: C, 53.05%, H, 3.21%; N, 18.01%. $C_{14}H_{10}N_4O_3S$, requires: C, 53.51%, H, 3.21%; N, 17.83%.

EXAMPLE 6 —
3-Carboxydibenzothiophene-5,5-dioxide

A. Preparation of 3-nitrodibenzothiophene-5,5-dioxide

To a mixture of acetic acid (77 ml) and sulphuric acid (77 ml) was added dibenzothiophene-5,5-dioxide (35.0 g), and the mixture cooled to 4° C. Addition of a total of 197 g. (131 ml) fuming nitric acid was begun, but in a short time the resulting paste became too thick to stir efficiently, and a further 77 ml. acetic acid was added. Local heating due to inefficient stirring was observed to occur, but the temperature of the reaction mixture was maintained at 4° C as far as was possible. When the addition was complete (ca. 20 min.), the mixture was stirred at 4° C for a further 30 min., and then poured into water. The crude nitrocompound was filtered off and recrystallised from dimethylformamide, m.p. 259° C.

B. Preparation of 3-aminodibenzothiophene-5,5-dioxide hydrochloride

A mixture of 3-nitrodibenzothiophene-5,5-dioxide (30.0 g), granulated tin (75 g), concentrated hydrochloric acid (425 ml) and water (750 ml) was boiled under reflux until all of the yellow nitro-compound was dissolved (2.5 hr.). The boiling solution was filtered through a sintered glass funnel, leaving undissolved tin (ca. 24 g), and the crystalline hydrochloride, which separated from the solution on cooling, was filtered off and dried at room temperature in vacuo, m.p. 235° C.

C. Preparation of 3-carboxydibenzothiophene-5,5-dioxide

To a vigorously stirred suspension of 3-aminodibenzothiophene-5,5-dioxide hydrochloride (27.35 g) in concentrated hydrochloric acid (40 ml) to which ice (150 g) had been added, was added at 0° C a solution of sodium nitrite (7.2 g) in water over 15 min. After the addition was complete, the mixture was stirred at 5° C for 10 min., and the solid material filtered off and washed with water. The solid was added to a solution of cuprous cyanide, prepared freshly from cupric sulphate pentahydrate (17.0 g) and potassium cyanide (8.84 g) in water (25 ml). The mixture was heated steadily to boiling over 20 min., cooled, and filtered. The solid residue was extracted with boiling ethanol (2 × 1 liter). Insoluble material was dicarded. The ethanol-soluble material, after evaporation of the solvent was boiled for 6 hrs. with potassium hydroxide (10 g) in water (150 ml) and ethanol (150 ml). The ethanol was evaporated off and water added, and some unchanged amine filtered off. The filtrate was acidified with hydrochloric acid and the precipitated acid filtered off and recrystallised from acetic acid, m.p. 312° C.

EXAMPLE 7 —
3-(5-Tetrazolyl)dibenzothiophene-5,5-dioxide

3-Aminodibenzothiophene-5,5-dioxide hydrochloride (11.80 g) was diazotised and converted to the crude nitrile as described in Example 24. The crude material was dissolved in chloroform and passed down a column of silica gel (500 g), eluting with chloroform. Evaporation of the solvent gave a mixture of amine and nitrile which was dissolved in dimethyl formamide (30 ml) and treated with sodium azide (1.3 g) and ammonium chloride (1.1 g). After heating on a steam bath for 6 hrs., the solution was diluted with water. The solid precipitate was filtered off and treated with aqueous sodium hydroxide solution (10 ml; 2.5%) at 80° C, filtered, and the filtrate acidified with hydrochloric acid. The product was filtered off, recrystallised from acetic acid and dried at 155°C/15 mm. Hg, m.p. 275° C (decomposed).

EXAMPLE 8 —
3-Carboxythioxanthene-10,10-dioxide

3-Carboxythioxanthone-10,10-dioxide (prepared as in Reference Preparation 4) (5.0 g), zinc wool (10.0 g) and mercuric acetate (0.2 g) in acetic acid (100 ml) were brought to the boil and concentrated hydrochloric acid (10 ml) was added. Vigorous evolution of hydrogen chloride occurred at first. After 2 hr., further hydrochloric acid (7 ml), was added and the mixture boiled under reflux for further 4 hr. It was then filtered while hot and poured on to ice and water. The precipitated product was filtered off and dried at 80° C in vacuo, m.p. 299°–248° C. Two recrystallisations from methanol gave the product m.p. 254° C.

EXAMPLE 9 —
2-(5-Tetrazolyl)phenoxathiin-10,10-dioxide

A. 2-(5-Tetrazolyl)phenoxathiin

Phenoxathiin (24.0 g) dissolved in carbon disulphide (500 ml) was treated with stannic chloride (34.0 g) dropwise over 30 min. with stirring. 1,1-Dichlorodimethyl ether (18.4 g) was then added dropwise over 15 min., and the mixture stirred at room temperature overnight. The carbon disulphide was distilled off and the residue treated with ice and concentrated hydrochloric acid. The product was extracted into benzene, washed with sodium bicarbonate solution, dried and evaporated to give oily product.

The crude phenoxathiin-2-aldehyde was dissolved in acetic acid (150 ml) and boiled with hydroxylamine hydrochloride (2.76 g) and sodium acetate (3.24 g) for 1.5 hr. Acetic anhydride (150 ml) was added, and the mixture boiled under reflux for 3 hr., cooled and filtered. The filtrate was poured into water and stirred for 1 hour to decompose the acetic anhydride, then extracted with chloroform, washed with water and sodium bicarbonate solution, dried, and evaporated to give crude 2-cyanophenoxathiin as an oil which solidified.

The crude cyano-compound was dissolved in dimethylformamide (35 ml) and heated with sodium azide (1.97 g) and ammonium chloride (1.77 g) for 6 hours. The mixture was poured into dilute hydrochloric acid and the crude product filtered off, dissolved in hot 4% sodium hydroxide (28 ml), filtered and the sodium salt of the tetrazole which crystallised out on standing filtered off and dried at 100° C, m.pt. above 320° C. The sodium salt was dissolved in hot water and acidified with excess hydrochloric acid. The free tetrazole was filtered off, and recrystallised from acetic acid, m.pt. 215° C (decomposes).

B. 2-(5-Tetrazolyl)phenoxathiin-10,10-dioxide 2-(5-Tetrazolyl)phenoxathiin (0.20 g) was dissolved in acetic acid (10.0 ml) and 30% hydrogen peroxide (2.0 ml) was added. The mixture was boiled under reflux for 2 hours, then cooled and poured into water. The precipitated product was filtered off and recrystallised from acetic acid, m.pt 168° C (decomposes).

EXAMPLE 10 —
3-Carboxythianthrene-5,5,10-trioxide

3-Carboxythianthrene-5,5-dioxide ((60 mg), acetic acid acid (2.0 ml) and 30% hydrogen peroxide (0.10 ml) were boiled under reflux for 10 mins., filtered and allowed to stand overnight at 0° C. 3-Carboxythianthrene-5,5,10-trioxide crystallised out, was filtered off and dried at 156° C at 2mm. Hg, m.p. 340°–343° C.

Analysis: Found C 50.38%; H 2.75%, Required for $C_{13}H_8O_5S_2$: C 50.66%; H 2.62%.

EXAMPLE A — Compression Coated Tablet

| | | |
|---|---|---|
| Core | 2-(5-Tetrazolyl)phenoxathiin-10,10-dioxide sodium salt | 100 mg |
| | Starch B.P. | 25 mg |
| | Magnesium Stearate B.P. | 2 mg |
| Coating | Lactose B.P. | 320 mg |
| | Starch B.P. | 50 mg |
| | Gelatin B.P. | 6 mg |
| | Magnesium Stearate B.P. | 4 mg |

Sodium Tetrazolyl salt and starch were granulated with water and dried. Magnesium stearate was added to the dried granule. Lactose and starch were granulated with a 10% w/v aqueous solution of gelatin and dried. Magnesium stearate was added to the dried granule. The granulated core was compressed with the granulated coating in a conventional compression moulding machine.

EXAMPLE B — Capsule

| | |
|---|---|
| 2-(5-Tetrazolyl)phenoxathiin-10,10-dioxide sodium salt | 200 mg |
| Lactose B.P. | 200 mg |
| Talc B.P. | 40 mg |

Sodium tetrazolyl salt, lactose and talc were brought into intimate admixture with one another and 440 mg of the resultant mixture was introduced into a size 0 hard gelatin capsule.

EXAMPLE C — Lotion For Topical Use

| | |
|---|---|
| 2-(5-Tetrazolyl)phenoxathiin-10, 10-dioxide sodium salt. | 1.5 g |
| Sorbitan Monolaurate | 0.6 g |
| Polysorbate 20 | 0.6 g |
| Cetostearyl Alcohol | 1.2 g |

-continued

| | | |
|---|---|---|
| Glycerin | | 6.0 g |
| Methyl Hydroxybenzoate | | 0.2 g |
| Purified Water B.P. | to | 100.0 ml |

The Methyl Hydroxybenzoate and Glycerin were dissolved in 70 ml. of the Water at 75° C. The Sorbitan Monolaurate, Polysorbate 20 and Cetosteary Alcohol were melted together at 75° C and added to the aqueous solution. The resulting emulsion was homogenised, allowed to cool with continuous stirring and the Sodium Tetrazolyl salt added as a solution in the remaining Water. The whole was stirred until homogeneous.

EXAMPLE D — Inhalation Aerosol

| | | |
|---|---|---|
| 2-(5-Tetrazolyl)phenoxathiin-10,10-dioxide (0.5–7.0 μm powder) | | 200 mg |
| Sorbitan Trioleate | | 100 mg |
| Saccharin Sodium (0.5 –7.0 μm powder) | | 5 mg |
| Menthol | | 2 mg |
| Trichlorofluoromethane | | 4.5 g |
| Dichlorodifluoromethane | to | 10.0 ml |

The Sorbitan Trioleate and Menthol were dissolved in the Trichlorofluoromethane. The Saccharin Sodium and Dioxide were dispersed in the mixture which was then transferred to a suitable aerosol canister and the Dichlorofluoromethane injected through the valve system. This composition provides 2 mg. of Acid in each 100 μl. dose.

EXAMPLE E — Lozenge

| | |
|---|---|
| 2-(5-Tetrazolyl)phenoxathiin-10,10-dioxide sodium salt. | 50 mg |
| Mannitol | 400 mg |
| Dextrose Monohydrate | 400 mg |
| Magnesium Stearate | 20 mg |

Granulated with solution of Polyvinylipyrrolidone 5% w/v in 25% w/v aqueous ethanol.

The Sodium Tetrazolyl salt was mixed with the Dextrose Monohydrate and Mannitol; granulated with the ethanolic Polyvinylpyrrolidone solution and then dried. The Magnesium Stearate was sifted on and the resulting mixture compressed to produce lozenges of the desired shape.

EXAMPLE F — Capsule

| | |
|---|---|
| 2-(5-Tetrazolyl)phenoxathiin-10,10-dioxide | 100 mg |
| Lactose | 100 mg |
| Maize Starch | 100 mg |
| Magnesium Stearate | 10 mg |

The ingredients were mixed together until homogeneous and 310 mg of the resulting mixture filled into each hard gelatin capsule.

EXAMPLE G — Tablet

| | |
|---|---|
| 2-(5-Tetrazolyl)phenoxathiin-10,10-dioxide | 500 mg |
| Maize Starch | 100 mg |
| Microcrystalline Cellulose | 75 mg |
| Magnesium Stearate | 10 mg |

Granulated with Polyvinylpyrrolidone 10% w/v in 50% w/v aqueous ethanol.

The Dioxide, Maize Starch and Microcrystalline Cellulose were mixed together, and granulated with the alcoholic Polyvinylpyrrolidone. The resulting granules were dried, and compressed to produce tablets, each tablet having a weight of approximately 690 mg.

EXAMPLE H — Foaming Non-aqueous Aerosol for Topical Use

| | |
|---|---|
| 2-(5-Tetrazolyl)phenoxathiin-10,10-dioxide (fine powder) | 5.0 g |
| Polyethylene Glycol 400 | 80.0 g |
| Propylene Glycol Monostearate, self-emulsifying | 5.0 g |
| Dichlorodifluoromethane (Propellant 12) | 4.0 g |
| Dichlorotetrafluoroethanethane (Propellant 114) | 6.0 g |

The Dioxide was dispersed in a mixture of the Propylene Glycol Monostearate, self-emulsifying, and the Propylene Glycol. An aerosol canister, was filled with the mixture, the valve sealed on and pressurisation effected by injecting the propellents through the valve.

EXAMPLE I — Foaming Aqueous Aerosol for Topical Use

| | | |
|---|---|---|
| Part A | 2-(5-Tetrazolyl)phenoxathiin,10,10-dioxide sodium salt | 2.2 g |
| | Triethanolamine | 3.2 g |
| | Glycerin | 4.7 g |
| | Polyvinylpyrrolidone | 0.3 g |
| | Purified Water B.P. | 81.0 g |
| Part B | Myristic Acid | 1.3 g |
| | Stearic Acid | 5.3 g |
| | Cetyl Alcohol | 0.5 g |
| | Lanolin | 0.2 g |
| | Isopropyl Myristate | 1.3 g |
| Propellents | Dichlorodifluoremethane | 4.0 g |
| | Dichlorotetrafluoroethane | 6.0 g |

The ingredients of Part B were melted together at 70° C. A solution of the ingredients of Part A in the Purified Water at the same temperature, was added to the melted ingredients of Part B. The resulting emulsion was homogenised and cooled to room temperature. The emulsion was filled into an aerosol canister, the valve crimped on and pressurisation effected by injecting the mixed propellents through the valve.

EXAMPLE J — Spray on Film for Topical Use

| | |
|---|---|
| 2-(5-Tetrazolyl)phenoxathiin-10,10-dioxide (fine powder) | 5.0 g |
| Polyethylene Glycol 600 | 0.8 g |
| Menthol | 0.01 g |
| Acetone | 43.5 g |
| Ethyl Alcohol Absolute | 45.69 g |
| Polyvinylpyrrolidone/Vinyl Acetate Copolymer (40:60) (PVP/VA) | 5.0 g |
| Dichlorodifluoromethane (Propellant 12) | 30.0 g |
| Dichlorotetrafluoroethane (Propellant 114) | 70.0 g |

The Polyethylene Glycol 600, Menthol and PVP/VA Copolymer were dissolved in a mixture of the Acetone and Ethyl Alcohol. The Dioxide was added and dispersed. The mixture was transferred to a suitable aerosol canister, the valve crimped on and pressurisation effected by injecting the mixture of propellents through the valve.

EXAMPLE K — Nasal Drops

| | | |
|---|---|---|
| 2-(5-Tetrazolyl)phenoxathiin-10,10-dioxide sodium salt | | 5.0 g |
| Chlorbutol | | 0.5 g |
| Purified Water B.P. | to | 100.0 ml |

The ingredients were dissolved in 95 ml. Purified water at room temperature. The resulting mixture was made up to 100mls with Purified Water and clarified by filtration.

EXAMPLE L — Eye Drops

| | | |
|---|---|---|
| 2-(5-Tetrazolyl)phenoxathiin-10,10-dioxide sodium salt | | 5.0 g |
| Methyl Hydroxybenzoate | | 0.10 g |
| Propyl Hydroxybenzoate | | 0.04 g |
| Purified Water B.P. | to | 100.00 ml |

The sodium tetrazolyl salt was dissolved in 70 ml. Purified Water at 75° C followed by the Methyl and Propyl Hydroxybenzoates. The resulting solution was allowed to cool and the solution made up 100 ml. with purified water. The solution was sterilised by filtration through a membrane filter 0.22 $\mu$m pore size and packed aseptically into suitable sterile containers.

EXAMPLE M — Powder Capsules for Inhalation

| | |
|---|---|
| 2-(5-Tetrazolyl)phenoxathiin-10,10-dioxide sodium salt (0.5–7.0 $\mu$m powder) | 4.0 mg |
| Lactose (30–90 $\mu$m powder) | 46.0 mg |

The powders were mixed until homogeneous and filled into suitably sized hard gelatin capsules, 50 mg of mixture per capsule.

EXAMPLE N — Injection Solution

| | | |
|---|---|---|
| 2-(5-Tetrazolyl)phenoxathiin-10,10-dioxide sodium salt | | 50.0 mg |
| Water for Injections B.P. | to | 1.0 ml |

The sodium tetrazolyl salt was dissolved in the bulk of the Water and then made up to volume and sterilised by filtration. The resulting solution was distributed into ampoules under aseptic conditions.

EXAMPLE O — Suppositories

| | |
|---|---|
| 2-(5-Tetrazolyl)phenoxathiin-10,10-dioxide | 200 mg |
| Suppository Base | 1.8 g |

The dioxide in fine powder form was dispersed into a little of the molten Suppository Base at 50° C. The dispersion was incorporated into the bulk of the base at the same temperature, allowed to cool at 42°–45° C. and poured into suitable 2g suppository moulds and allowed to set at 15°–20° C. Suppository Bases were Massa Esterinum C and Witten H Suppository Compound.

EXAMPLE P — Dispersible Tablet

| | Per tablet |
|---|---|
| 2-(5-Tetrazolyl)phenoxathiin-10,10-dioxide | 200.00 mg |
| Maize Starch | 40.00 mg |
| Primojel (Trade name: sodium starch glycollate (125 $\mu$m powder) | 50.00 mg |
| Dicalcium Phosphate Dihydrate | 50.00 mg |
| Sodium Carboxymethyl Cellulose | 2.00 mg |
| Dioctyl Sodium Sulphosuccinate | 0.25 mg |
| Sodium Saccharin | 5.00 mg |
| Microcrystalline Cellulose | 50.00 mg |
| Magnesium Stearate | 3.00 |
| | 400.25 mg |

The Dioxide half of the Maize Starch, the Primojel and Dicalcium Phosphate were mixed together and then granulated with a solution of Sodium Carboxymethyl Cellulose, Dioctyl Sodium Sulphosuccinate and Sodium Saccharin in a suitable volume of 50% Ethyl Alcohol. The granules were dried, the remaining Maize Starch, the Microcrystalline Cellulose and the Magnesium Stearate were blended in and the resulting mixture compressed into tablets each having a weight of 400.25 mg.

What we claim is:

1. The method of preventing the symptoms of an allergic condition of a mammal having an allergic condition which comprises administering to said mammal a prophylactically effective amount of a tricyclic compound:

2-(5-tetrazolyl)phenoxathiin-10,10-dioxide; or a pharmaceutically acceptable salt thereof, said allergic condition being selected from the group consisting of asthma, allergic rhinitis, conjunctivitis, urticaria and eczema.

2. The method of claim 1 wherein the tricyclic compound is administered as a powder having a particle size in the range of 0.5 to 7$\mu$.

3. The method of claim 2 wherein the tricyclic compound is administered at a dose of 5$\mu$g. to 0.5mg. per kilogram body weight of said mammal.

4. A method as claimed in claim 1 wherein said tricyclic compound or salt thereof is administered by the oral route.

5. A method as claimed in claim 4 wherein said tricyclic compound or salt thereof is administered at a dose of 1 to 50mg. per kilogram body weight of said mammal.

6. A method as claimed in claim 5 wherein said allergic condition is allergic asthma.

7. A method as claimed in claim 5 wherein said allergic condition is hay fever.

8. The method of preventing the symptoms of allergic asthma effecting a mammal having allergic asthma comprising the administration to said mammal of a prophylactic dose of 10 to 40 mg. per kilogram body weight of said mammal of a tricyclic compound selected from the group consisting of 2-(5-tetrazolyl)phenoxathiin-10,10-dioxide and a pharmaceutically acceptable salt of said compound.

9. The method of claim 8 wherein said salt is a sodium salt.

10. The method of preventing the symptoms of an allergic condition of a mammal having an allergic condition which comprises administering to said mammal a prophylactically effective amount of a tricyclic compound of formula I

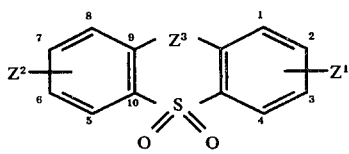

wherein the tricyclic compound of formula I Z¹ is a substituent in the 1-, 2-, 3-, or 4-position and is 5-tetrazolyl, a 5-(1-alkyl) tetrazolyl group or a 5-(2-alkyl) tetrazolyl group in which the alkyl groups have 1 to 6 carbon atoms and are each optionally substituted by hydroxy; $Z^2$ is hydrogen or a substituent in the 5-, 6-, 7- or 8-position and has the same values as the group $Z^1$ as defined above or is halogen, or an alkyl or alkoxy group each containing from 1 to 6 carbon atoms; and $Z^3$ is oxygen; or a pharmaceutically acceptable salt thereof: said allergic condition selected from the group consisting of asthma, allergic rhinitis, conjunctivitis, urticaria and eczema.

11. The method of preventing the symptoms or asthma or allergic rhinitis in a mammal having astham or allergic rhinitis which comprises administering to said mammal a phophylactically effective amount of a compound of formula I

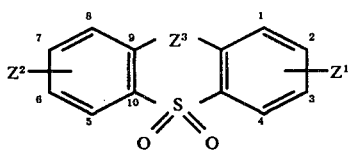

wherein $Z^1$ is a substituent in the 1-, 2-, 3-, or 4-position and is 5-tetrazolyl, 5-(1-alkyl)tetrazolyl, or 5-(2-alkyl) tetrazolyl, in which the alkyl groups have 1 to 6 carbon atoms and are each optionally substituted by a hydroxyl group;

$Z^2$ is hydrogen or a substituent in the 5-, 6-, 7- or 8-position selected from the values of the group $Z^1$ as defined above is is halogen, or an alkyl or alkoxy group each containing 1 to 6 carbon atoms; and $Z^3$ is oxygen;

or a pharmaceutically acceptable salt thereof.

12. The method of preventing the symptoms of asthma or allergic rhinitis in a mammal having asthma or allergic rhinitis which comprises administering in a form for oral or pulmonary administration a prophylactically effective amount of the compound 2-(5-tetrazolyl)phenoxathiin-10,10-dioxide or a pharmaceutically acceptable salt thereof.

13. A pharmaceutical composition for the prevention of the symptoms of asthma or allergic rhinitis and which is in a form for oral or pulmonary administration which comprises a prophylactically effective amount of the compound 2-(5-tetrazolyl)phenoxathiin-10,10-dioxide or a pharmaceutically acceptable salt thereof.

14. A pharmaceutical composition for use in the prevention of the symptoms of asthma, allergic rhinitis, conjunctivitis, urticaria or eczema comprising a prophylactically effective non-toxic amount of a tricyclic compound of formula I

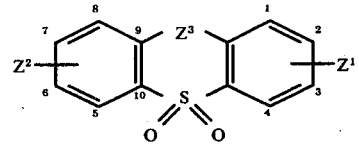

wherein $Z^1$ is a substituent in the 1-, 2-, 3-, or 4-position and is 5-tetrazolyl, 5-(1-alkyl)tetrazolyl, or 5-(2-alkyl)-tetrazolyl, in which the alkyl groups have 1 to 6 carbon atoms are each optionally substituted by a hydroxyl group;

$Z^2$ is hydrogen or a substituent in the 5-, 6-, 7- or 8-position selected from the values of the group $Z^1$ as defined above or is halogen, or an alkyl or alkoxy group each containing 1 to 6 carbon atoms; and $Z^3$ is oxygen;

or a pharmaceutically acceptable salt thereof;.

in association with a pharmaceutically acceptable carrier therefor.

15. A pharmaceutical composition for the prevention of the symptoms of asthma or allergic rhinitis comprising an effective asthma or allergic rhinitis prophylactic amount of a tricyclic compound of formula I

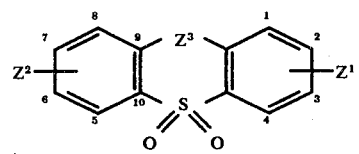

wherein $Z^1$ is a substituent in the 1-, 2-, 3-, or 4-position and is 5-tetrazolyl, 5-(1-alkyl)tetrazolyl, or 5-(2-alkyl) tetrazolyl, in which the alkyl groups have 1 to 6 carbon atoms and are each optionally substituted by a hydroxyl group;

$Z^2$ is hydrogen or a substituent in the 5-, 6-, 7- or 8-position selected from the values of the groups $Z^1$ as defined above or is halogen, or an alkyl or alkoxy group each containing 1 to 6 carbon atoms; and $Z^3$ is oxygen;

or a pharmaceutically acceptable salt thereof;

in association with a pharmaceutically acceptable carrier therefor.

16. A pharmaceutical composition for use in preventing the symptoms of asthma, allergic rhinitis, conjunctivitis, urticaria or eczema comprising a prophylactically effective non-toxic amount of 2-(5-tetrazolyl)phenoxathiin-10,10-dioxide or a pharmaceutically acceptable salt thereof in association with a pharmaceutically acceptable carrier therefor.

17. A tablet for use in preventing the symptoms of an allergic condition being selected from the group consisting of asthma, allergic rhinitis, conjuntivitis, urticaria and eczema and said tablet containing as an active ingredient from 50 to 500 mg. of a tricyclic compound selected from the group consisting of 2-(5-tetrazolyl)phenoxathiin-10,10-dioxide; and a pharmaceutically acceptable salt of said compound.

* * * * *